US00PP20954P2

(12) United States Plant Patent
Hammett

(10) Patent No.: US PP20,954 P2
(45) Date of Patent: Apr. 27, 2010

(54) *DAHLIA* PLANT NAMED 'BEST BETT'

(50) Latin Name: *Dahlia variabilis*
Varietal Denomination: BEST BETT

(76) Inventor: Keith Hammett, 488 C Don Buck Road, Massey, Auckland (NZ) 0614

( * ) Notice: Subject to any disclaimer, the term of this patent is extended or adjusted under 35 U.S.C. 154(b) by 0 days.

(21) Appl. No.: 12/228,984

(22) Filed: Aug. 18, 2008

(51) Int. Cl.
*A01H 5/00* (2006.01)

(52) U.S. Cl. ..... Plt./321

(58) Field of Classification Search ..... Plt./321
See application file for complete search history.

*Primary Examiner*—Annette H Para

(57) ABSTRACT

A new cultivar of *Dahlia* named 'BEST BETT' that is distinguishable by upright habit, dark brown to black divided leaves and flower buds, and vivid amber colored star-shaped blossoms. In combination these traits set 'BEST BETT' apart from all other existing varieties of *Dahlia* known to the inventor.

2 Drawing Sheets

Genus: *Dahlia.*

Species: *variabilis.*

Figure 1:
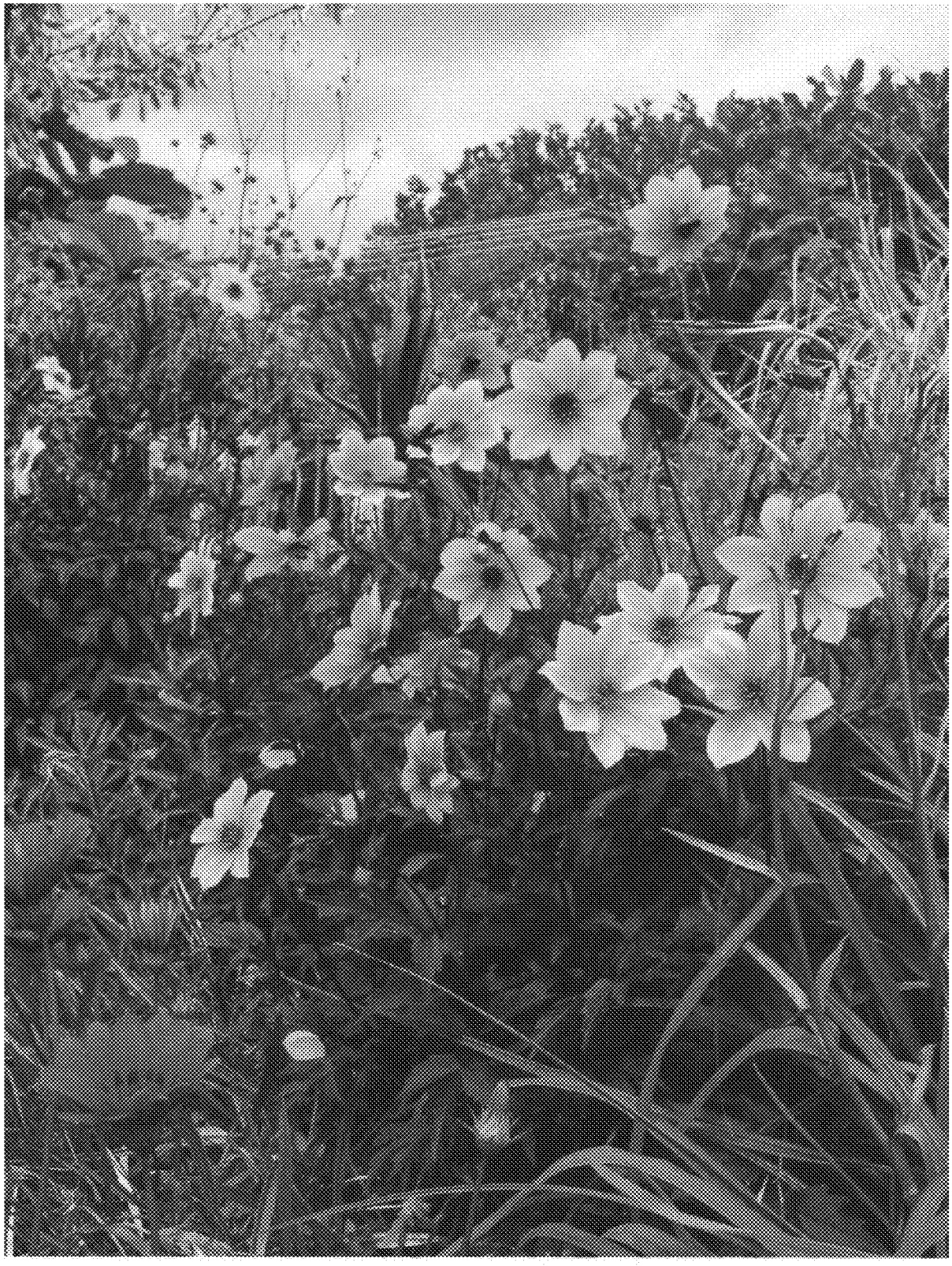

Denomination: 'BEST BETT'.

BACKGROUND OF THE INVENTION

The present invention relates to a new and distinct cultivar of *dahlia* that is grown for use in mixed combinations, beds and the landscape. The new invention is known botanically as *Dahlia variabilis* and will be referred to hereinafter by the cultivar name 'BEST BETT'. The specific epithet *variabilis* represents a hybrid seedling line that came from crossing various original wild species in the early 1800s, and refers to the species' wide range of flower color and shapes. The genus *Dahlia* is in the family Compositae. The flower of 'BEST BETT' is classified as a "single" form blossom and exhibits a single row of ray flowers surrounding a central cluster of disk florets.

'BEST BETT' is the product of a formal breeding program established by the inventor in 1990 at the inventor's nursery in Auckland, New Zealand. The inventor selected his variety *Dahlia variabilis* 'Scarlet Fern' (U.S. Plant Pat. No. 18,989) as the female parent and *Dahlia variabilis* 'White Hallelujah' (unpatented) as the male parent. The parents were placed in isolation and insect pollinated. Seed was collected from the female parent and coded as 71500/03, then sown with the intention of making a selection from the seedlings that resulted.

'BEST BETT' was selected in 2004 based on the criteria of leaf color and clarity of flower color. Selection was conducted by the inventor, in Auckland, New Zealand. The unique traits that distinguish the new *Dahlia* variety named 'BEST BETT' from other varieties of the same genus are mahogany-black divided leaves and profusions of vivid amber star-shaped blossoms. The new *Dahlia* named 'BEST BETT' is distinguishable from the parents by the clarity of bloom color and darkness of the leaves.

'BEST BETT' exhibits upright habit, large dark brown to black buds, fragrant apricot flowers, and dark brown to black foliage. The large star-shaped blossoms bloom in summer and fall. Cultural conditions include full sun, regular water and rich well-draining potting soil. 'BEST BETT' is hardy to USDA Zone 8 and grows to 1.25 m in height and 0.9 m in width at maturity.

The first asexual reproduction of 'BEST BETT' was conducted in 2004 in Auckland, New Zealand. The method of asexual propagation utilized was tissue culture. Since that time under careful observation, the distinguishing characteristics have been determined stable, uniform, and to be reproduced true to type in subsequent generations of asexual propagation.

SUMMARY OF THE INVENTION

The following traits have been repeatedly observed and represent the distinguishing characteristics of the new *Dahlia* cultivar named 'BEST BETT'. These traits in combination distinguish 'BEST BETT' from all other existing varieties of *Dahlia* known to the inventor. 'BEST BETT' has not been tested under all possible conditions and phenotypic differences may be observed with variations in environmental, climatic, and cultural conditions, however, without any variance in genotype.

1. 'BEST BETT' exhibits upright habit.
2. 'BEST BETT' exhibits dark brown to black divided leaves.
3. 'BEST BETT' exhibits large dark brown to black buds and dark purple stems.
4. 'BEST BETT' exhibits fragrant vivid amber star-shaped blossoms.
5. 'BEST BETT' blooms in the summer and fall.
6. 'BEST BETT' grows to 1.25 m in height and 0.9 m in width at maturity.
7. 'BEST BETT' is hardy to USDA Zone 8.

BRIEF DECRIPTION OF THE DRAWINGS

Figure 2:
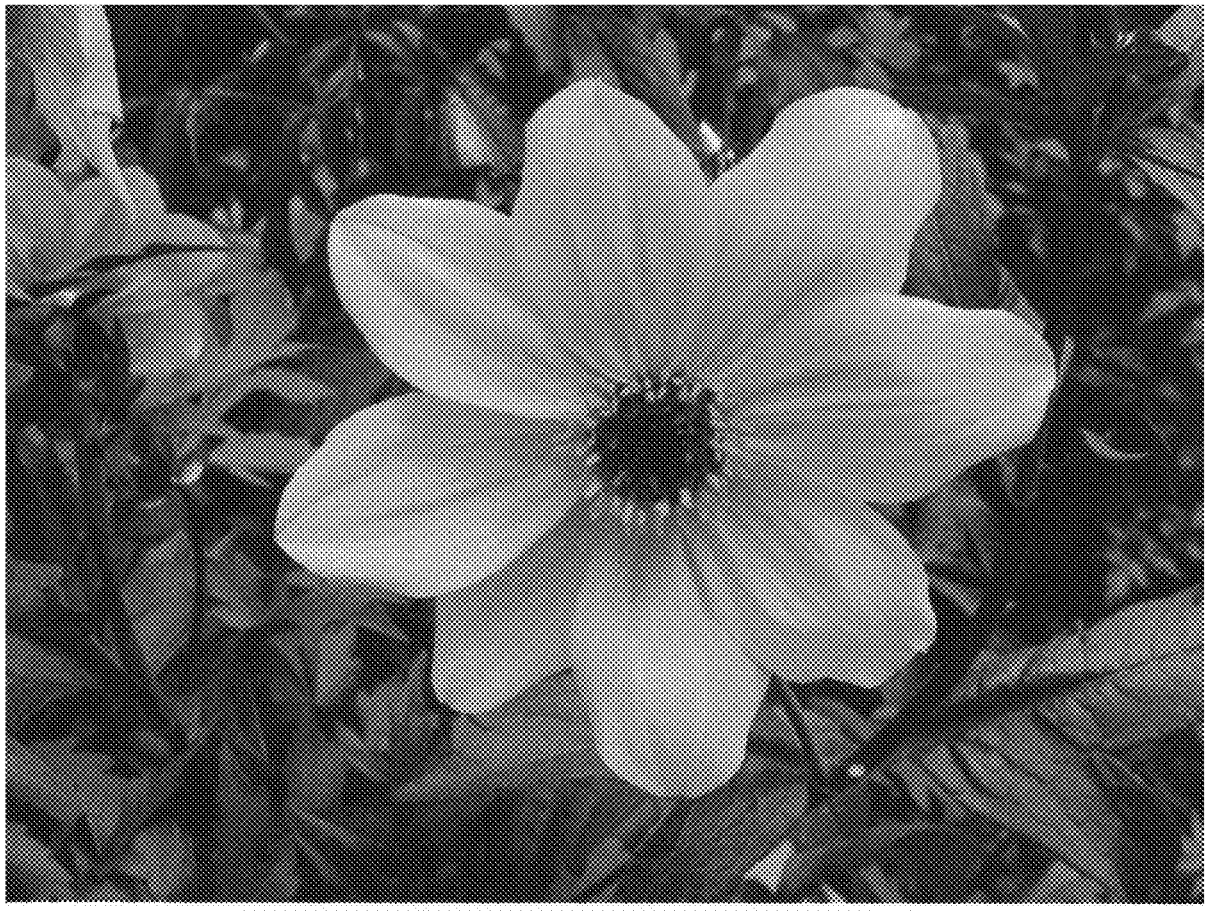

The accompanying color drawings labeled FIG. 1 and FIG. 2 illustrate the overall appearance of the new *Dahlia* cultivar named 'BEST BETT' showing the colors as true as is reasonably possible to obtain in colored reproductions of this type. Colors in the photographs may differ from the color values cited in the detailed botanical description, which accurately describes the actual colors of the new *Dahlia* variety named 'BEST BETT'.

The drawing labeled FIG. 1 depicts an entire plant in bloom.

The drawing labeled FIG. 2 depicts a close-up view of a flower.

The drawings were made of 18 months old plants using conventional techniques and although colors may appear different from actual colors due to light reflectance they are as accurate as possible by conventional photography.

BOTANICAL DESCRIPTION OF THE PLANT

The following is a detailed botanical description of the new *Dahlia* cultivar named 'BEST BETT'. Observations, measurements, values and comparisons were collected in Arroyo Grande Calif. from 18 months old plants which have been grown in 2-litre containers. Color determinations arc in accordance with the 2001 Royal Horticultural Society Colour Chart from London England, except where general color terms of ordinary dictionary significance are used. Growing requirements are similar to the species.

Botanical classification: *Dahlia variabilis* 'BEST BETT'.

Family: Compositae.

Genus: *DAHLIA*.

Species: *variabilis*.

Denomination: 'BEST BETT'.

Common name: *Dahlia*.

Parentage: *Dahlia variabilis* 'BEST BETT' is a seedling selection made from plants grown from seed which resulted from the cross-pollination of the following parents:

*Female parent.*—*Dahlia variabilis* 'Scarlet Fern' (U.S. Plant Pat. No. 18,989).

*Male parent.*—*Dahlia variabilis* 'White Hallelujah' (unpatented).

Propagation method: Tissue culture.

Rooting system: Fine and fibrous.

Vigor: Vigorous.

Habit: Upright habit.

Use: For use in mixed combinations, beds and the landscape.

Type: Perennial.

Dimensions in first season: 0.6 m. in height and 0.6 m. in width.

Dimensions at maturity: 1.2 m. in height and 0.9 m. in width.

Cultural requirements: Grow in full sun with regular water, and well-draining potting soil.

Pest susceptibility: Susceptible to aphids.

Disease susceptibility: Susceptible to mildew in highly humid conditions.

Hardiness: USDA Zone 8.

Stem:

*Color.*—N186B.

*Dimensions.*—45 cm in length and 0.4 cm in width.

*Shape.*—Cylindrical.

*Surface.*—Glabrous.

*Internode length* (*average*).—7 cm.

Foliage:

*Type.*—Evergreen.

*Leaf arrangement.*—Opposite.

*Leaf division.*—Simple.

*Leaf dimensions* (*average*).—11.50 cm in length and 9 cm in width.

*Leaf color* (*adaxial surface*).—N186A.

*Leaf color* (*abaxial surface*).—189A.

*Margin.*—Ciliate and pinnatisect.

*Leaf shape.*—Hastate.

*Leaf base.*—Attenuate.

*Leaf apex.*—Apiculate.

*Leaf venation pattern.*—Pinnate.

*Vein color* (*abaxial and adaxial surfaces*).—N186C.

*Leaf surfaces* (*abaxial surfaces*).—Slightly puberulent.

*Leaf surfaces* (*adaxial surfaces*).—Glabrous.

*Leaf attachment.*—Petiolate.

*Leaf fragrance.*—None observed.

*Petiole shape.*—Sulcate.

*Petiole dimensions.*—2.50 cm to 4 cm in length and 0.10 cm in width.

*Petiole color.*—N186B.

*Presence of stipules or spines.*—None observed.

Inflorescence:

*Inflorescence type.*—Terminal: Flowers classified as "single" form, with single row of ray flowers surrounding a central cluster of disk florets.

*Aspect.*—Facing upward and outward.

*Inflorescence quantity.*—15–20 per 2-litre container plant.

*Dimensions of inflorescence* (*average*).—9 cm in diameter and 6.50 cm in depth.

*Inflorescence shape.*—Radiate with center disk.

*Blooming seasons.*—Summer and fall.

*Peduncle.*—Dimensions (average): 10 cm in length and 0.40 cm. in diameter. Shape: Cylindrical. Surface: Glabrous. Color: N186B.

*Bud.*—Shape: Oblate. Dimensions (average): 2 cm in height and 1.75 cm in diameter. Surface: Glabrous. Appearance: Semi-glossy. Color: 187A. Apex: Obtuse. Base: Truncate.

*Ray florets.*—Quantity per inflorescence: 8. Dimensions (average): 4.50 cm. in length and 2.50 cm. in width. Form: Petaloid. Shape: Obovate. Surface (adaxial and abaxial): Glabrous. Arrangement: Radiate. Apex: Obtuse. Base: Cuneate. Margin: Entire. Color (adaxial and abaxial surfaces): 1A. Vein color (adaxial and abaxial surfaces): 187C. Vein pattern: Parallel.

*Disk florets.*—Quantity of disk florets: In excess of 90 per inflorescence. Dimensions: 1.75 cm in length and 0.10 cm in width. Color: 187A. Petals: 8 in number. Petals fused or unfused: Fused. Petal apex: Acute. Petal surface (ventral and dorsal surfaces): Glabrous. Receptacle dimensions: 1 cm in depth and 1.60 cm in diameter. Receptacle surface: Glabrous. Receptacle color: 187A.

*Phyllary.*—Inner phyllary: Number: 8. Shape: Elongated ovate. Dimensions: 2.50 cm in length and 0.7 cm in width. Color (adaxial and abaxial surfaces): Between N199B and N199C. Texture: Scarious. Appearance: Translucent. Apex: Subacute. Base: Truncate. Margin: Entire. Surface (adaxial and abaxial): Glabrous. Outer phyllary: Number: 5 in number. Shape: Obovate. Dimensions: 1.50 cm. in length and 0.75 cm. in width. Color (adaxial and abaxial surfaces): N187A and N189A both present. Form: Reflexed. Apex: Obtuse. Base: Truncate. Margin: Entire. Surface (adaxial and abaxial): Glabrous.

*Self-cleaning or persistent.*—Self-cleaning.

*Fragrance of inflorescence.*—Perfumed.

Reproductive organs:

*Stamens.*—5 in number.

*Stamen attachment.*—Filament adnate to ventral surface of corolla.

*Stamen length.*—6 mm in length.

*Stamen color.*—166A.

*Anther.*—Connate.

*Anther color:* 166A.

*Pollen.*—Present.

*Quantity.*—Large amount.

*Pollen color.*—N163D.

*Pistil.*—One present.

*Pistil length.*—9 mm in length.

*Stigma dimensions.*—3 mm in length and 4.50 mm in width.

*Stigma form.*—Plumose.

*Stigma color.*—N163A.

*Stigma shape.*—Bifurcate.

*Ovary position.*—Inferior.

*Ovary color.*—150D.

*Ovary shape.*—Rotund.

*Ovary dimensions.*—2 mm in width and 3 mm in height.

Seed: None observed to date.

The invention claimed is:

1. A new and distinct cultivar of *Dahlia* plant named 'BEST BETT' as described and illustrated herein.

* * * * *